United States Patent [19]

Buckberg et al.

[11] Patent Number: 5,021,045
[45] Date of Patent: Jun. 4, 1991

[54] RETROGRADE VENOUS CARDIOPLEGIA CATHETERS AND METHODS OF USE AND MANUFACTURE

[75] Inventors: Gerald D. Buckberg, Los Angeles, Calif.; Robert J. Todd, Salt Lake City, Utah

[73] Assignee: Research Medical, Inc., Salt Lake City, Utah

[21] Appl. No.: 187,230

[22] Filed: Apr. 28, 1988

[51] Int. Cl.$^5$ ............................................. A61M 29/02
[52] U.S. Cl. .................................... 604/53; 604/96; 604/102
[58] Field of Search .................................. 604/51–53, 604/96–99, 102, 103, 264, 280; 128/344; 606/194

[56] References Cited

U.S. PATENT DOCUMENTS

| | | | |
|---|---|---|---|
| 2,164,926 | 7/1939 | Kleine | 604/170 |
| 4,210,478 | 7/1980 | Shoney | 604/103 |
| 4,290,428 | 9/1981 | Durand et al. | 604/97 |
| 4,413,989 | 11/1983 | Schjeldahl et al. | 604/96 |
| 4,459,977 | 7/1984 | Pizon et al. | 128/344 |
| 4,610,661 | 9/1986 | Possis et al. | 604/52 |
| 4,689,041 | 8/1987 | Corday et al. | 604/96 |
| 4,714,460 | 12/1987 | Calderon | 604/53 |
| 4,753,637 | 6/1988 | Horneffer | 604/53 |
| 4,784,638 | 11/1988 | Ghajar et al. | 604/280 |
| 4,804,358 | 2/1989 | Karcher et al. | 604/53 |
| 4,850,969 | 7/1989 | Jackson | 604/96 |

FOREIGN PATENT DOCUMENTS 249338 12/1987 European Pat. Off. ............. 604/53

OTHER PUBLICATIONS

USCI Catalog, 1967–68, p. 41.
ACMI Catalog, 4/1972, p. 18, Pelham, N.Y.
Gerald D. Buckberg, M.D., "Reterograde Pulmonary Venous Pressure Measurement–Fact or Artifact?", The Journal of Thoracic and Cardiovascular Surgery, vol. 59, No. 3, pp. 393–406, Mar. 1970.
Philippe Menasche, M.D. et al., "Retrograde Coronary Sinus Perfusion: A Safe Alternative for Ensuring Cardioplegic Delivery in Aortic Valve Surgery", The Annals of Thoracic Surgery, vol. 34, No. 6, Dec. 1982, pp. 647–658.
Gerald D. Buckberg, M.D., "Strategies and Logic of Cardioplegic Delivery to Prevent, Avoid, and Reverse Ischemic and Reperfusion Damage", The Journal of Thoracic and Cardiovascular Surgery, 1987, vol. 93, pp. 127–139.
Donald G. Mulder et al., "Myocardial Protection During Aortic Valve Replacement", The Annals of Thoracic Surgery, vol. 21, No. 2, Feb. 1976, pp. 123–130.

(List continued on next page.)

*Primary Examiner*—Stephen C. Pellegrino
*Assistant Examiner*—Ralph A. Lewis
*Attorney, Agent, or Firm*—Workman, Nydegger & Jensen

[57] ABSTRACT

This invention relates to a retrograde cardioplegia catheter and its method of use. The catheter contains two lumens, an infusion lumen through which the cardioplegic solution flows and a pressure sensing lumen for monitoring the fluid pressure at the point where the solution exits the catheter. A slightly tapered, self-filling balloon is secured to the distal end of the catheter. Also, located at the distal end of the catheter is a soft, rounded tip to prevent damage to the sensitive intimal tissues of the coronary sinus. A stylet having a predetermined curve at the distal end and a handle at the proximal end is removably located within the infusion lumen. The predetermined curve at one end of the stylet enables the cardioplegia catheter to be inserted quickly and accurately within the coronary sinus through a very small incision made in the right atrium. After the catheter is securerd in place, the stylet is withdrawn. The catheter remains in position for the duration of the operation in order to periodically readminister the cardioplegia solution.

79 Claims, 4 Drawing Sheets

OTHER PUBLICATIONS

Jorge Solorzano, M.D. et al., "Retrograde Coronary Sinus Perfusion for Myocardial Protection During Cardiopulmonary Bypass", The Annals of Thoracic Surgery, vol. 25, No. 3, Mar. 1978, pp. 201-208.

Philippe Menasche et al., "Retrograde Coronary Sinus Perfusion", Roberts Textbook Myocardial Protection in Cardiac Surgery, printed 1987, Chapter 15, pp. 251-262.

Charles C. Reed, Diane K. Clark, Chapter 19, "Cannulation", Chapter 23.

"Myocardial Protection", Cardiopulmonary Perfusion, Texas Medical Press, Inc., Houston, Tex., 1975.

Dr. Dwight C. McGoon, "Coronary Perfusion", Journal of Thoracic and Cardiovascular Surgery, vol. 70, No. 6, p. 1025, Dec. 1975.

International Working Group on Coronary Sinus Interventions, Newsletter, vol. 1, No. 3, Oct. 1987.

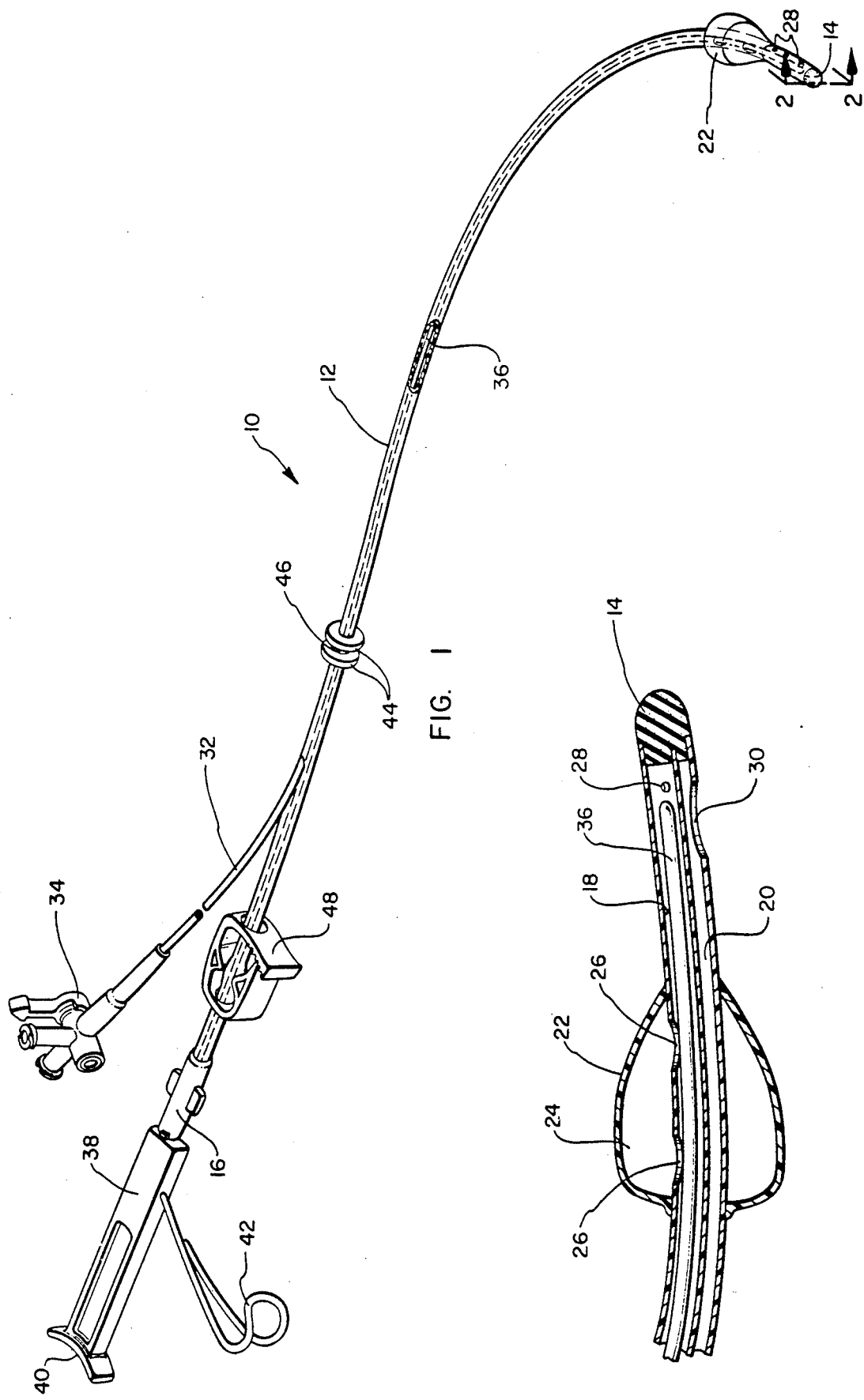

RETROGRADE VENOUS CARDIOPLEGIA CATHETERS AND METHODS OF USE AND MANUFACTURE

BACKGROUND

1. The Field of the Invention

The present invention is directed to retrograde cardioplegia catheters and the methods of their use and manufacture. More particularly, the catheters of the present invention are designed for rapid and accurate insertion into the coronary sinus and for retrograde administration of cardioplegia with maximum effectiveness and minimum tissue damage.

2. The Prior Art

Since the early days of cardiac surgery, it has been recognized that in order to provide the optimum surgical conditions when operating on the heart, it is necessary to interrupt the normal operation of the heart. For obvious reasons, an arrested, flaccid heart is preferred during a cardiac surgical procedure over a beating heart with blood s flowing through it. Thus, in order to be able to efficiently perform cardiac surgery, it is often necessary to use cardiopulmonary-bypass techniques and to isolate the heart from its life-giving blood supply.

It has been found that many deaths occurring after cardiac surgery are due to acute cardiac failure. At first, it was believed that the heart was simply beyond repair and that the operation had failed to correct the problem. Later, it was discovered that many of these postoperative deaths were due to new, and often extensive, perioperative (during or within 24 hours after the surgical procedure) myocardial necrosis (death of the heart tissue). Furthermore, many patients who survived were found to have suffered myocardial necrosis to a significant degree, thereby resulting in low cardiac blood output.

It is now known that myocardial necrosis occurs because the energy supply or reserve of the cardiac muscle cells is inadequate to supply the needs of the heart. The availability of oxygen dramatically affects the cell s ability to satisfy these energy requirements. For example, anaerobic metabolism of glucose produces two (2) moles of adenosine triphosphate ("ATP") per mole of glucose (as well as harmful acid metabolites), whereas aerobic metabolism of glucose produces thirty-six (36) moles of ATP per mole of glucose. Therefore, one of the primary goals of myocardial s preservation techniques during surgery is to reduce myocardial oxygen consumption.

Myocardial oxygen consumption is significantly reduced by stopping the electromechanical work of the heart. The oxygen demands of the beating empty heart at 37° C. are four to five times those of the arrested heart (i.e., 4-5 ml/100-gm/min compared with 1 ml/100-gm/min). Buckberg, G. D., "Strategies and Logic of Cardioplegic Delivery to Prevent, Avoid, and Reverse Ischemic and Reperfusion Damage," 93 *The Journal of Thoracic and Cardiovascular Surgery*, 127, 136 (Jan. 1987) (hereinafter referred to as: Buckberg, "Strategies and Logic of Cardioplegic Delivery").

Oxygen consumption can be reduced further by cooling the heart. For example, the oxygen requirements of the arrested heart at 20° C. are 0.3 ml/100-gm/min and are reduced to only 0.15 ml/100-gm/min at 10° C. On the other hand, the oxygen requirements of the beating or fibrillating heart at comparable temperatures, are 2-3 ml/100-gm/min. Buckberg, "Strategies and Logic of Cardioplegic Delivery" at 129.

The normal heart receives its blood supply through the left and right coronary arteries which branch directly from the aorta. Generally, the veins draining the heart flow into the coronary sinus which empties directly into the right atrium. A few veins, known as thebesian veins, open directly into the atria or ventricles of the heart.

One of the early methods utilized to protect the myocardium during surgery was normothermic perfusion of the empty beating heart. This method was utilized in an effort to maintain the heart, as near as possible, in normal conditions during surgery. Although the procedure eliminated the problem of blood flow, dissection and suturing were still difficult to perform because of the firmness of the myocardium and the beating of the heart. Additionally, it was found that a significant amount of damage still occurred to the myocardium when this procedure was utilized.

A second method which was developed to protect the myocardium was intermittent cardiac ischemia with moderate cardiac hypothermia. This method requires that the entire body be perfused at a temperature of from 28° C. to 32° C., thus slowing all bodily functions, including those of the heart. The heart is fibrillated before aortic crossclamping to stop the beating. The surgeon can then operate for approximately fifteen to twenty-five (15-25) minutes, after which time the heart beat is necessarily resumed for three to five (3-5) minutes. This procedure proved to be an inefficient method for performing operations and had many attendant dangers, including the fibrillation of the heart.

A third method which has been utilized is profound hypothermic cardiac ischemia. This method requires that the temperature of the heart be lowered to about 22° C. by the infusion of a cooled perfusate and/or by filling the pericardium with cold saline solution. One of the major disadvantages of this technique is that the heart continues to fibrillate, exhausting the heart's stored energy. As a result, the heart becomes acidotic, which over time causes irreversible muscle damage.

A fourth method which has been developed to preserve the myocardium during surgery is the infusion of a cold cardioplegic fluid to cool and stop the beating of the heart After the initial infusion, the heart is reperfused approximately every thirty (30) minutes to maintain the cool, dormant state of the heart.

The use of cardioplegia to protect the myocardium has proven the most advantageous method of those used to date. Cardioplegia, which literally means "heart stop," may be administered in an antegrade manner (through arteries in the normal direction of blood flow), in a retrograde manner (through veins opposite the normal blood flow direction), or in a combination of retrograde and antegrade administration. Cardioplegic solutions, typically containing potassium, magnesium procaine, or a hypocalcemic solution, stop the heart by depolarizing cell membranes.

Cardioplegia may be induced immediately after extracorporeal circulation has begun, provided that the pulmonary artery is collapsed to attest to the adequacy of venous return. In normal antegrade cardioplegia, a single venous return catheter is inserted in the right atrium to transfer the blood from the body to the heart-lung machine which a single needle is inserted into the aorta beneath the clamp through which the cardioplegic solution is administered. The cardioplegic solution flows through the coronary arteries in the normal blood flow direction.

If aortic insufficiency exists (imperfect closure of the aortic valve) or the patient is undergoing aortic valve replacement, then direct cannulation of the coronary arteries is necessary to perform antegrade cardioplegia. In this technique the aortic root is opened (using the procedure called "aortotomy") and perfusion catheters are inserted into both the left and right coronary ostia.

Care must be taken to avoid mechanical injury to the coronary ostia which could produce the serious complications of coronary ostial stenosis (i.e. constricting of the coronary ostia). Ostial stenosis requires reparative surgery and can be quite hazardous due to obstruction of the coronary arteries. Moreover, it is a nuisance to have perfusion catheters present within the limited operative field during aortic valve replacement. The inconvenience and time consumed by positioning perfusion catheters have led to dissatisfaction with direct coronary perfusion.

The foregoing risks and inconvenience of direct coronary cannulation may be avoided by using the retrograde cardioplegia technique. For this reason, some surgeons select retrograde cardioplegia as the preferred method of myocardial protection during aortic valve replacement.

Retrograde cardioplegia is conventionally administered by inserting a balloon catheter within the coronary sinus, inflating the balloon to stop the normal fluid flow into the right atrium, and perfusing the cardioplegic solution backwards through the coronary veins. In order to insert the catheter into the coronary sinus, the right heart must be isolated. To isolate the right heart, both the superior and inferior venae cavae must be tied and each must be cannulated. Once the right heart is isolated, the right atrium may be opened without allowing air to enter the circulatory system, thereby reducing the risk of systemic air embolization.

With the right atrium open, the catheter is visually inserted into the coronary sinus and hand-held while the cardioplegic solution is administered. The right atrium is then closed. This process must be repeated each time cardioplegic solution is administered during the operation. See Buckberg, "Strategies and Logic of Cardioplegic Delivery" at 132-33.

Retrograde cardioplegia is more complicated than antegrade cardioplegia because it requires right heart isolation, right atriotomy (i.e. opening the right atrium), and hand-holding the catheter during perfusion. Furthermore, retrograde cardioplegia may result in undesirable consequences.

For example, the atriotomy may lead to heart arrhythmia, and repeated cannulation may substantially injure the coronary sinus. In addition, high perfusion pressure or the failure to periodically allow normal venous drainage may damage the coronary veins and microcirculatory system causing edema. For these reasons, some surgeons completely avoid retrograde cardioplegia.

Nevertheless, there are some situations where retrograde cardioplegia is advisable over antegrade. For example, antegrade cardioplegia produces nonhomogeneous cooling and cardioplegic maldistribution in cases of myocardial ischemia and diffuse coronary disease. Antegrade cardioplegia does not adequately protect those areas of the heart downstream from coronary artery obstructions.

Several surgical graft techniques have been developed to circumvent coronary artery obstructions. In almost all of these techniques, cardioplegic solution is delivered down the grafts after they are completed. The graft is first attached to the coronary artery below the blockage, thereby leaving the other end of the graft open through which the cardioplegic solution can be administered. The open end of the graft is then attached to the aorta. Unfortunately, the area of the heart downstream of the obstruction does not receive any cardioplegic protection until after the graft is attached.

In the case of diffuse coronary artery disease, not all of the coronary blockages receive grafts. Therefore, the areas that are not grafted receive very minimal protection. In these situations, only retrograde cardioplegia can adequately protect those areas of the heart downstream from the coronary blockages.

Recently, some surgeons have begun using the internal mammary artery as the preferred graft for use on patients with coronary artery disease. It has been found that the internal mammary artery provides a superior long-term graft over the customary vein grafts (e.g., saphenous vein grafts). However, because the internal mammary artery remains proximally intact and insertion of a needle into the mammary artery would severely damage the artery, antegrade cardioplegia cannot be delivered through the internal mammary artery.

Many surgeons choose not to use internal mammary grafts in patients who have more severe forms of heart disease because antegrade cardioplegia is not available to protect the heart, notwithstanding the graft's superiority. Because antegrade cardioplegia does not adequately protect the heart downstream of the graft, that part of the heart muscle may be permanently damaged, resulting in a mortality or a very complicated, prolonged convalescence.

Although retrograde cardioplegia would provide adequate protection for those patients undergoing an internal mammary graft, surgeons often opt to use antegrade cardioplegia in combination with the inferior saphenous vein graft in order to avoid the cumbersome retrograde cardioplegia technique. The net result is that the sick patient receives a good short-term benefit by surviving the operation. But many years later, the patient has an inferior graft which may require additional surgery.

Furthermore, it has been found that by combining retrograde and antegrade cardioplegia many of the limitations inherent in the two protection strategies may be overcome so that a more uniform degree of myocardial hypothermia and complete regional and global left and right ventricular functional recovery is possible. Nevertheless, clinical adoption of retrograde cardioplegic techniques, alone or in combination with antegrade techniques, has been slow despite evidence of its usefulness. The principle reason for this delay in clinical acceptance seems to stem from the more cumbersome operative technique that is required to employ retrograde cardioplegia.

Most cardiac operations in adult patients are performed with single venous cannulation. Thus, the need for double cannulation of the venae cavae and isolation of these vessels, right atriotomy, and hand-holding of the catheter in the coronary sinus are all additional surgical procedures required in order to perform retrograde cardioplegia. These additional procedures, combined with possible isolation of the pulmonary artery, slower time to arrest, and possible large volumes of the cardioplegic solution needed to fill the right heart have limited the acceptance of current retrograde techniques.

In summary, retrograde cardioplegia often can provide superior myocardial protection over antegrade cardioplegia alone and the combination of retrograde cardioplegia and antegrade cardioplegia can provide superior myocardial protection than either technique alone. Yet there is substantial resistance by many surgeons to take advantage of the benefits of retrograde cardioplegia because it complicates an already complex surgical procedure.

From the foregoing, it will be appreciated that what is needed in the art are apparatus and methods for performing retrograde cardioplegia which are simple and effective so that the advantages of retrograde cardioplegia can be readily utilized by surgeons.

Additionally, it would be a significant advantage over the art to provide apparatus and methods for performing retrograde cardioplegia which do not require right atrial isolation, right atriotomy, and repeated cannulation of the catheter.

It would be another advancement in the art to provide a retrograde cardioplegia catheter which can be quickly and accurately inserted within the coronary sinus with relatively little trauma to the patient.

It would be yet another advancement in the art to provide apparatus and methods for performing retrograde cardioplegia which allow surgeons to safely use the internal mammary graft without making the surgical procedure cumbersome.

The foregoing, and other features and objects of the present invention, are realized in the retrograde cardioplegia catheter apparatus and method which are disclosed and claimed herein.

BRIEF SUMMARY AND OBJECTS OF THE INVENTION

The present invention is directed to retrograde cardioplegia catheters and their methods of use and manufacture. The catheters of the present invention include two lumens—a large lumen through which the cardioplegic solution flows and a smaller lumen which may be connected to a pressure sensing device for monitoring the fluid pressure at the point where the cardioplegic solution exits the catheter into the coronary sinus.

A self-filling balloon is secured near the distal end of the catheter. In the preferred embodiment of the present invention, the self-filling balloon is slightly tapered. A plurality of apertures in the larger lumen open into the self-filling balloon. These apertures allow the cardioplegic solution to fill the balloon while the fluid is flowing, but when the fluid stops, the balloon empties.

A low-trauma tip occludes the distal end of the catheter The tip is rounded and soft to prevent damage to the sensitive intimal tissues of the coronary sinus. The larger lumen includes plurality of small openings located between the low-trauma tip and the self-filling balloon which allow the cardioplegic solution to exit the catheter.

A removable stylet, or "introducer," is located within the large lumen. The stylet has a predetermined curve at the distal end thereof and a handle at the proximal end which permit rapid and accurate positioning of the catheter within the coronary sinus. The stylet enables the catheter to be inserted within the coronary sinus through a very small incision made in the right atrium, as opposed to a relatively large incision (about three (3) centimeters long) necessary when the current retrograde cardioplegic technique is used.

The predetermined curve at the proximal end of the stylet permits rapid and accurate positioning of the catheter within the coronary sinus. The catheter is then simply secured in place with a purse string suture, and the stylet is withdrawn from the catheter. Once securely positioned, the catheter remains in place for the duration of the operation. It will be appreciated, that the method of using the present invention avoids right atrial isolation, right atriotomy, repeated cannulation of the catheter, and hand-holding of the catheter during retrograde perfusion of the cardioplegic solution.

As the cardioplegic solution flows through the large lumen of the catheter of the present invention, the self-filling balloon fills to seal the coronary sinus and to prevent the solution from flowing into the right atrium. The small lumen is operatively connected to a pressure sensing device which monitors the pressure within the coronary sinus. If the pressure becomes too great, the flow of cardioplegic solution is automatically stopped, allowing the balloon to empty and the solution to drain into the right atrium.

It is, therefore, an object of the present invention to provide apparatus and methods for performing retrograde cardioplegia which are simple and effective so that the advantages of retrograde cardioplegia can be readily utilized by surgeons.

Another important object of the present invention is to provide apparatus and methods for performing retrograde cardioplegia which do not require right atrial isolation, right atriotomy, and repeated cannulation of the apparatus.

An additional object of the present invention is to provide a retrograde cardioplegia catheter which may be quickly and accurately positioned within the coronary sinus.

Still another object of the present invention is to provide apparatus and methods for performing retrograde cardioplegia which allow surgeons to safely use the lifesaving internal mammary graft without making the surgical procedure cumbersome.

These and other objects and features of the present invention will become more fully apparent from the following description and appended claims taken in conjunction with the accompanying drawings.

BRIEF DESCRIPTION OF THE DRAWINGS

FIG. 1 is a perspective view of one presently preferred embodiment within the scope of the present invention.

FIG. 2 is a cross-sectional view of the distal end of the embodiment illustrated in FIG. 1 taken along line 2—2 of FIG. 1.

DETAILED DESCRIPTION OF THE PREFERRED EMBODIMENTS

A. The Retrograde Cardioplegia Catheters

Figure 3:
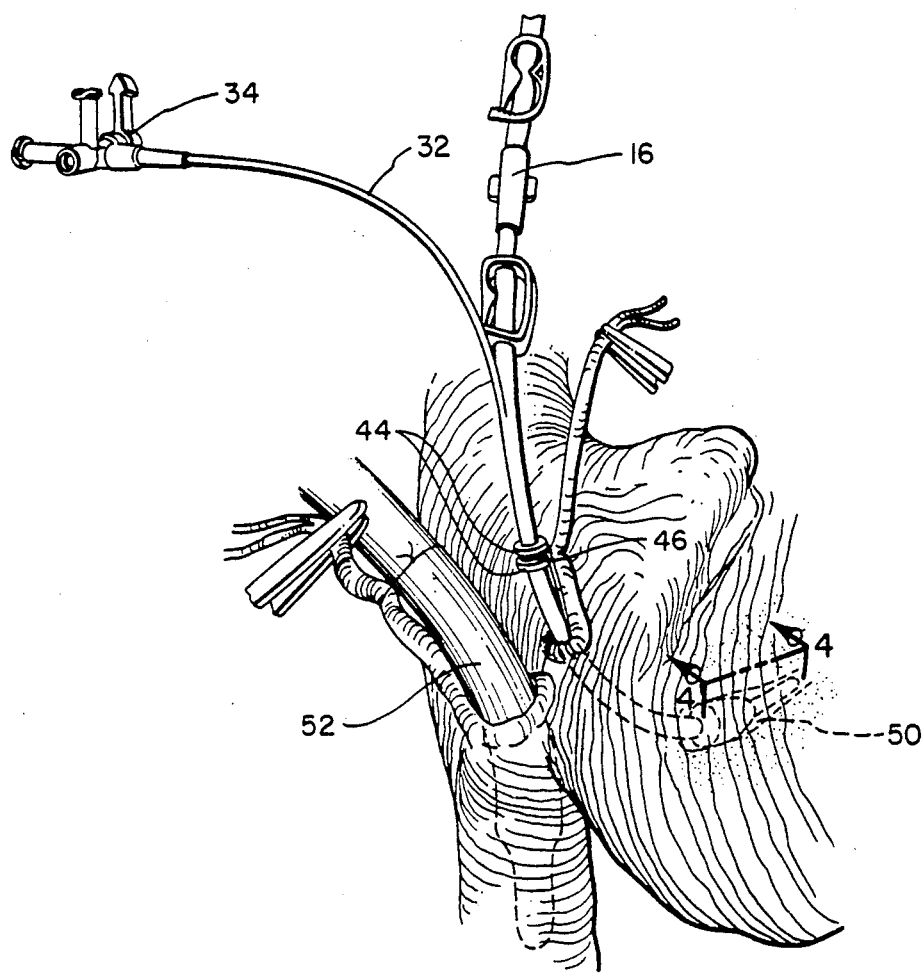
FIG. 3 is a perspective view illustrating a preferred embodiment of the retrograde cardioplegic catheter of the present invention, when inserted within the coronary sinus of the heart.

Reference is now made to the drawings wherein like parts are designated with like numerals throughout. Referring first to FIGS. 1 and 2, one presently preferred embodiment of an apparatus within the scope of the present invention is illustrated and generally designated 10.

Catheter 10 is particularly designed for the retrograde venous administration of cardioplegic solutions. The apparatus includes a flexible cannula 12 having a soft, rounded tip 14 at the distal end and a coupling device 16 at the proximal end for attaching the catheter to a cardioplegic solution source. The cardioplegic solution would typically be provided through either a volumetric pump or a bag of solution within a pressure cuff.

Flexible cannula 12 contains two lumens: an infusion lumen 18 for introducing the cardioplegic solution into the coronary sinus and a pressure-sensing lumen 20 for monitoring the fluid pressure within the coronary sinus.

The flexible cannula is preferably constructed of a material which retains its flexibility after prolonged exposure to temperatures of at least about 0° C. In one current preferred embodiment, flexible cannula 12 is constructed of medical-grade polyvinyl chloride, having a softness of about 75 to 85 durometer, Shore-A. Other suitable materials, may also be used to construct flexible cannula 12, such as medical-grade silicone and polyurethane.

It is important that the flexible cannula be flexible enough to manipulate and position within the coronary sinus, but also have sufficient rigidity and structural integrity to not collapse or bend to cut off flow of the cardioplegic solution during use. In addition, the flexible cannula should be soft enough to compress or deflect when pressed against the coronary sinus, thereby protecting the coronary should not be so soft that a tie holding it in place occludes the cannula.

As best illustrated in FIG. 2, soft, rounded tip 14 occludes the end of both infusion lumen 18 and pressure-sensing lumen 20. The soft rounded tip is preferably constructed of a material which will minimize the trauma and the risk of intimal damage to the coronary sinus and other heart tissues during insertion and use.

In one presently preferred embodiment of the present invention, the rounded tip is constructed of medical-grade polyvinyl chloride, having a softness of about 55 to 60 durometer, Shore A. Other suitable materials may be used to construct the rounded tip such as silicone and polyurethane.

In one presently preferred embodiment, the rounded tip is constructed with two small appendages formed to fit within the infusion and pressure-sensing lumens. The fit between the rounded tip and the outer wall of flexible cannula 12 should be smooth to reduce the possibility of an exposed uneven edge injuring sensitive heart tissues.

The rounded tip is preferably solvent bonded to the distal end of the flexible cannula. It is important that the solvent maintains a seal or bond between the rounded tip and the end of the lumens during use. Additionally, the solvent should not create a hard surface which could cause trauma during insertion, use, or removal. Cyclohexanone is the presently preferred solvent, but other solvents such as butanone (methyl ethyl keton), tetrahydrofuran ("THF"), and methylene chloride are possible suitable substitutes.

A self-filling balloon 22 is located near the distal end of flexible cannula 12, slightly proximal from rounded tip 14. Self-filling balloon 22 forms an inner chamber 24 inside the balloon and outside cannula. In one embodiment of the present invention, the distal end of the self-filling balloon is located approximately 2.0 cm to approximately 6.0 cm back from the rounded tip. Such an embodiment permits rounded tip 14 to be inserted far into the coronary sinus, yet still permit the self-filling balloon to seal the coronary sinus. For most purposes, the distal end of the self-filling balloon is preferably located about 2.0 cm to a bout 3.5 cm back from the rounded tip.

One preferred method of attaching the self-filling balloon to the flexible cannula is solvent bonding with tetrahydrofuran, though other solvents such as dimethylformamide ("DMF"), acetone, and cyclohexanone, for example, could be substituted. The balloon is attached to the flexible cannula according to techniques well-known in the art.

In the preferred embodiment of the present invention, the balloon is slightly tapered, increasing in diameter from the distal end to the proximal end of the balloon. The taper allows cardioplegic solution to be infused into the more distal branches of the coronary sinus, thereby providing thorough cardioplegic protection. A cylindrically shaped balloon might readily occlude the ostia of the more distal branches of the coronary sinus which may be as close as 0.5 cm from the entry of the sinus into the right atrium. If the ostia are occluded, then portions of the heart upstream from the ostia would not receive cardioplegic protection.

A taper in the range of from about 25° to about 35°, measured from the longitudinal axis of the flexible cannula has been found to be suitable. Other larger or smaller tapers may be used. However, if the taper is too great, then the balloon is difficult to properly insert and position within the coronary sinus, and there is more likelihood of trauma to the tissues as the cannula is inserted and positioned. If the taper is too small, then the balloon becomes too long to fit within the coronary sinus and still engage the walls.

In addition, it has been found that a balloon taper within the range of the present invention performs a unique self-centering function which facilitates quick and accurate placement of the catheter within the coronary sinus.

A plurality of balloon apertures 26 in infusion lumen 18 allow the flowing cardioplegic solution to inflate the balloon. The balloons of most balloon catheters known in the art expand and collapse depending upon the fluid pressure within the balloon compared with the fluid pressure outside the balloon. It has been found that the pressure required to inflate conventional balloon catheters to seal the coronary sinus often results in an excessive infusion pressure. In addition, the low operating fluid pressures used in connection with the present invention could not adequately inflate conventional balloon catheters.

In response to this problem, the self-filling balloon of the present invention is constructed so that it is not necessary for the balloon to expand significantly from its unfilled state in order to seal the coronary sinus. Thus, upon filling, the balloon becomes turgid but not significantly distended beyond the balloon's original shape.

The self-filling balloon preferably has a cross-sectional diameter which is slightly larger than the cross-sectional diameter of the coronary sinus. A typical adult coronary sinus has a diameter in the range of from about 1.4 cm to about 1.6 cm. Hence, in most individuals, a balloon having a cross-sectional diameter in the range of from about 1.6 cm to 2.0 cm will work.

In one current preferred embodiment of the present invention, the balloon has a cross-sectional diameter from about 1.7 cm to about 1.8 cm. Upon insertion within the coronary sinus, when the balloon has not been filled with cardioplegic solution the balloon becomes slightly wrinkled about its outer periphery due to the smaller diameter of the cardioplegic solution the balloon is filled and becomes turgid in order to sealingly engage the walls of the coronary sinus.

It will be appreciated that the coronary sinus of pediatric patients will be somewhat smaller than that of an adult patient. As a result, a retrograde cardioplegia catheter designed for pediatric use is necessarily designed so that the a self-filling balloon has a diameter to fit within the coronary sinus of the patient.

The total cross-sectional area of balloon apertures 26 is preferably between approximately 1.5 to approximately 5 times the cross-sectional area of infusion lumen 18 to facilitate rapid filling and emptying of the balloon. In the presently preferred embodiment within the scope of the present invention, the total cross-sectional area of apertures 26 is about 2 to 3 times the cross-sectional area of the infusion lumen.

The embodiment illustrated FIGS. 1 and 2 shows two balloon apertures 26. The number of openings is dependent on various factors. On the one hand, the total cross-sectional area of the apertures must be large (relative to the cross-sectional area of the infusion lumen) in order for the balloon to be self-filling. On the other hand, too many apertures or too large or improperly configured apertures can compromise the structural integrity of the catheter, thereby causing the tube to bend and/or collapse during use and inhibit flow of cardioplegic solution through the catheter.

Thus, there is a balance between having enough properly shaped and sized openings to create a large total cross-sectional area and having too many openings which weaken the catheter. In addition, the difficulty of cutting holes in the infusion lumen without damaging the pressure-sensing lumen must be considered in determining the number of balloon openings 26. Hence, while more or fewer apertures can be readily made to work, two have been found to be satisfactory for most situations.

A plurality of small infusion lumen outlets 28 located between the balloon and the rounded tip allow the cardioplegic solution to exit the catheter. It has been found that the total cross-sectional area of infusion lumen outlets 28 should be less than the cross-sectional diameter of the balloon openings 26. In the presently preferred embodiment, the total cross-sectional area of infusion lumen outlets 28 is in the range from about twenty-five percent (25%) to about seventy-five percent (75%) the cross-sectional area of infusion lumen 18. In the presently preferred embodiment, the total cross-sectional area of infusion lumen outlets 28 is approximately fifty percent (50%) the cross-sectional area of infusion lumen 18.

In one preferred embodiment of the present invention there are six infusion lumen outlets, three on each side of infusion lumen 18 spaced about 0.2 inches apart and starting about 0.5 cm back from the rounded tip, each outlet having a diameter of about 0.03 inches which provides for a total cross-sectional area of the infusion lumen outlets of about fifty percent (50%) the total cross-sectional area of the infusion lumen. The cross-sectional area of the infusion lumen is in the range of from about 0.007 square inches to 0.009 square inches, and preferably about 0.008 square inches.

The primary factor to consider in determining the number and size of the infusion lumen outlet is the resulting total cross-sectional area percentage compared to the cross-sectional area of the balloon aperture and/or the infusion lumen. However, care should be taken so that the infusion lumen outlets are not so small that the cardioplegic solution exits the catheter in a jet-like flow which could harm the coronary sinus. To further reduce any potential trauma to the coronary sinus from the exiting cardioplegic solution, the infusion lumen outlets are preferably bored in the infusion lumen at an angle so that the cardioplegic solution exits the catheter in a forward direction.

Because the total cross-sectional area of balloon aperture 26 is preferably substantially greater than the total cross-sectional area of infusion lumen outlets 28, the fluid pressure of flowing cardioplegic solution within the balloon inner chamber is greater than the fluid pressure at the point the solution exits the catheter. In this way, the self-filling balloon automatically fills as cardioplegic solution flows through the infusion lumen. When cardioplegic solution flow stops, the balloon empties as the solution drains into the coronary sinus.

A sensing lumen orifice 30 near the distal end of pressure-sensing lumen 20 permits sensing of the fluid pressure at the point where the cardioplegic solution exits the catheter within the coronary sinus. It is important to closely monitor the pressure within the coronary sinus, because if the fluid pressure exceeds a predetermined maximum pressure (as discussed in greater detail hereinafter), tissue damage and edema to the coronary sinus and other heart tissues will likely result. The cross-sectional area of sensing lumen orifice 30 is preferably greater than the cross-sectional area of pressure-sensing lumen 20. In the presently preferred embodiment, the cross-sectional area of sensing lumen orifice 30 is in the range from about 2 to about 3 times the cross-sectional area of pressure-sensing lumen 20.

A pressure-sensing feed line 32, which is an extension of pressure-sensing lumen 20, branches from flexible cannula 12 near the proximal end of the catheter. A three-way stopcock 34 is located at the proximal end of pressure-sensing feed line 32. The three-way stopcock permits coupling to a pressure-sensing device at one setting, removing air from the pressure-sensing lumen at a second setting, and sealing the feed line at the third setting. The pressure-sensing lumen is occluded at a point proximal to the point feed line 32 branches from the flexible cannula to prevent introduction of cardioplegic solution into the pressure-sensing lumen.

A removable stylet 36 is located within flexible cannula 12, the stylet has at the distal end a predetermined curve and at the proximal end a stylet handle 38. The stylet handle contains a thumb rest 40 located at the proximal end thereof. A loop 42 extends outward from the stylet handle in the same general direction as the predetermined curve. The stylet is preferably constructed out of a rigid material, such as a metal rod.

A pair of rings 44 are located just distal of the point where pressure-sensing feed line 32 branches from flexible cannula 12. Rings 44 define a suture groove 46 therebetween. The suture groove enables the catheter to be tied in place after insertion within the coronary sinus. It is important to tie the catheter in position to minimize longitudinal movement of the catheter in the coronary sinus.

A clamp 48 is located on flexible cannula 12 between rings 44 and the point were the pressure sensing feed line branches from the flexible cannula. This clamp seals the infusion lumen and inhibits relative movement of the stylet vis-a-vis the catheter while the catheter is being inserted with the coronary sinus.

B. Methods of Using the Retrograde Cardioplegia Catheter

Referring now to FIG. 3, catheter 10 is inserted into a small incision which has been made in the right atrium. The incision is preferably less than one centimeter long and is about 1 inch to about 2 inches from the entrance of the coronary sinus 50. A pulse-string suture is placed to seal the right atrium incision around the catheter.

Because the right atrium is not completely opened by the methods of the present invention, it is not necessary to isolate the right heart by tying and cannulating both venae cavae. This not only simplifies the surgical procedure, but also reduces the trauma experienced by the patient. In addition, because the incision in the right atrium is very small, there is little risk that the patient will develop a heart arrhythmia which often occurs when the right atrium is opened.

The curved stylet enables the catheter to be accurately positioned within the coronary sinus through such a small incision in the right atrium without visually seeing the coronary sinus. The unique stylet handle configuration gives the surgeon many options for holding the stylet and inserting the catheter within the coronary sinus. These options vary depending on the operating room condition, the position of the patient's heart, and the surgeon's own preference.

In one use of the present invention, the surgeon, standing on the patient's right side, presses the right index finger against loop 42, the right ring finger against stylet handle 38, and the thumb against thumb rest 40. In this position, the catheter is quickly inserted within the coronary sinus with a slight twist of the wrist by moving the index finger towards oneself and the thumb away from oneself while keeping the ring finger relatively stationary.

If the surgeon is standing on the patient's left side, it may be preferable to place the ring finger against the loop and the index finger against the stylet handle. The catheter can be quickly inserted by moving the ring finger towards oneself and the thumb away from oneself while keeping the index finger relatively stationary. The above grips may be reversed and modified if the surgeon prefers using the left hand.

Once in position, the catheter is secured with a purse-string suture around the incision in the right atrium. The stylet is then withdrawn, and suture groove 46 is tied to the tourniquet tube of the purse-string suture as shown in FIG. 3 to prevent longitudinal movement of the catheter in the coronary sinus. The catheter remains in its proper position through the duration of the surgical procedure. Thus, there is no need to either repeatedly insert the catheter within the coronary sinus or hand-hold the catheter during the procedure. In this way, trauma to the coronary sinus is reduced and simplification of the procedure are achieved.

When the catheter is inserted within the coronary sinus, stylet 36 seals the infusion lumen and three-way stopcock 34 seals the pressure-sensing lumen. After insertion, the air within both the infusion and pressure sensing lumens is vented.

To accomplish this, a syringe is attached to coupling device 16 in order to remove any air from the infusion lumen. Clamp 48 is then closed until the coupling device is attached to a cardioplegic solution source. Similarly, the three-way stopcock is adjusted to permit removal of air from the pressure-sensing lumen. The three-way stopcock is then attached to a pressure-sensing device.

Conventional cardioplegic solutions known in the art may be used in performing retrograde cardioplegia within the scope of the present invention. The same cardioplegic solution source used for performing retrograde cardioplegia may be used for performing retrograde and antegrade cardioplegia in combination.

Generally, regardless of the type of surgical procedure involved, a venous return catheter 52 shown in FIG. 3 would be required to enable extracorporeal circulation. Therefore, the method for retrograde administration of cardioplegic solutions disclosed herein does not significantly complicate the surgical procedure compared to present retrograde cardioplegia methods.

Figure 4:
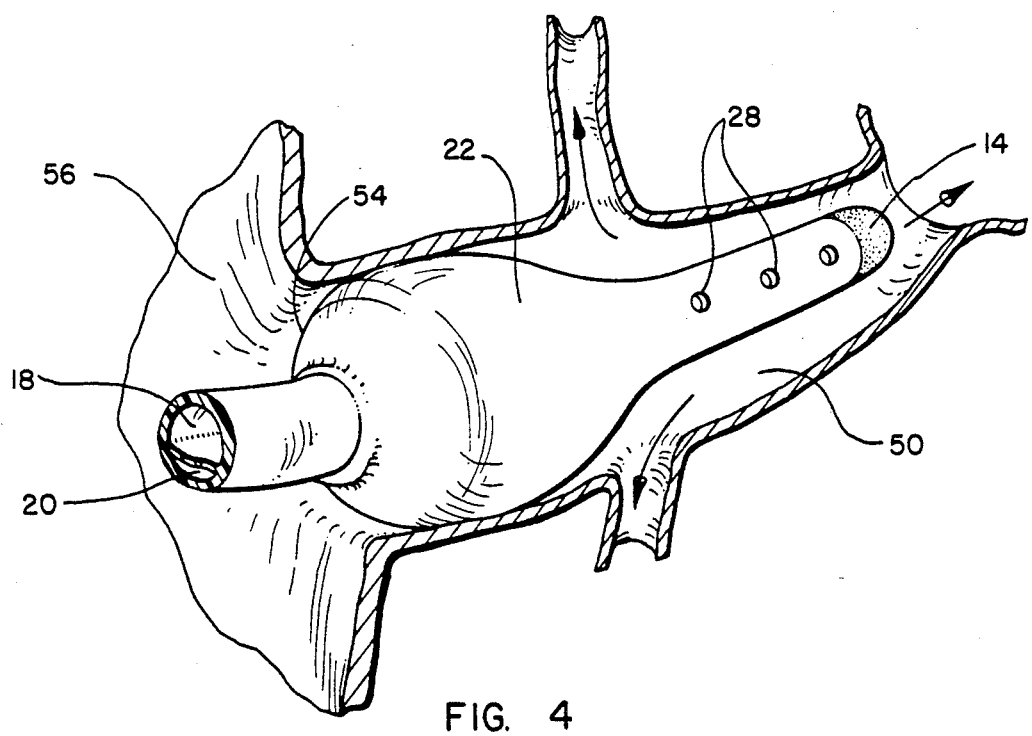
FIG. 4 is a partial cross-sectional perspective view of the retrograde cardioplegic catheter within the coronary sinus taken along line 4—4 of FIG. 3.

FIG. 4 illustrates the proper placement of the catheter within coronary sinus 50. Self-filling balloon 22 is positioned just within coronary sinus orifice 54 of right atrial wall 56. As the cardioplegic solution flows through infusion lumen 18, the fluid flows through openings 26 to fill the self-filling balloon. Upon filling, the self-filling balloon is turgid but not significantly distended beyond its original shape.

During infusion of the cardioplegic solution, the fluid pressure within the coronary sinus is monitored. If the pressure rises above a predetermined maximum pressure, then infusion of the cardioplegic solution is stopped. Once infusion of the cardioplegic solution stops, the balloon empties to allow normal antegrade flow into the right atrium. The catheter does not need to be removed to allow for normal antegrade flow.

It has been found that if the pressure within the coronary sinus exceeds about 60 mm Hg, venular damage and hemorrhage may result. It will be appreciated that this maximum pressure may vary from patient to patient, but this pressure is a conservative maximum pressure. Therefore, the pressure within the coronary sinus is preferably maintained below approximately 50 mm Hg in order to provide a margin of error.

The pressure within the inner chamber of the self-filling balloon will be somewhat greater than the pressure within the coronary sinus due to the pressure drop associated with the infusion lumen outlets. Since excessive pressure within the balloon may cause the balloon to expand and injure the coronary sinus, the pressure within the balloon is preferably maintained below about 150 mm Hg.

Because of the pressure drop through the infusion lumen and associated connectors, the pressure within the self-filling balloon is less than the system pressure at the cardioplegic solution source. If the cardioplegic solution contains blood, then care should be taken to maintain the fluid pressure within the entire cardioplegia system below approximately 300 mm Hg. It has been found that blood subjected to pressures exceeding about 300 mm Hg is subject to hemolysis.

The cardioplegic solution flow rate should be adjusted to maintain a safe pressure within the coronary sinus, within the inner chamber of the self-filling balloon, and throughout the cardioplegia system. The flow rate is preferably maximized within the above constraints.

Under anticipated operating conditions, the flow rate of cardioplegic solution will be preferably in the range from about 200 ml/min to about 300 ml/min. The flow rate may vary depending upon the extent of coronary obstructions within the patient's heart and upon other heart conditions such as heart temperature and muscular tone of the coronary circulatory system.

Because the catheter is positioned within the coronary sinus during the entire surgical procedure, additional cardioplegic solution may be readily administered as needed. There is no need to repeatedly insert the catheter within the coronary sinus or to hand hold the catheter during infusion. Thus, the present invention facilitates periodic infusion and its associated benefits. Periodic infusion is necessary because all hearts receive some noncoronary collateral blood flow which tends to wash away the cardioplegic solution. Periodic infusion of cardioplegic solution at about twenty to thirty minute intervals counteracts noncoronary collateral washout.

During lengthy cardiac surgery, periodic infusion of the cardioplegic solution provides a number of significant benefits. For example, periodic infusion (1) maintains arrest, (2) restores desired levels of hypothermia, (3) buffers acidosis, (4) washes acid metabolites away which inhibit continued anaerobiosis, (5) replenishes high-energy phosphates if the cardioplegia solution is oxygenated, (6) restores substrates depleted during ischemia, and (7) counteracts edema. Buckberg, "*Strategies and Logic of Cardioplegic Delivery*" at 131.

The present invention is particularly useful in delivering retrograde venous cardioplegia in combination with antegrade cardioplegia. A combination of retrograde and antegrade cardioplegia provides more homogeneous distribution of the cardioplegic solution to the right and left ventricles, stops the heart faster, and leads to more complete regional recovery of the jeopardized muscle and the global left and right ventricles than use of antegrade cardioplegia alone.

Figure 5:
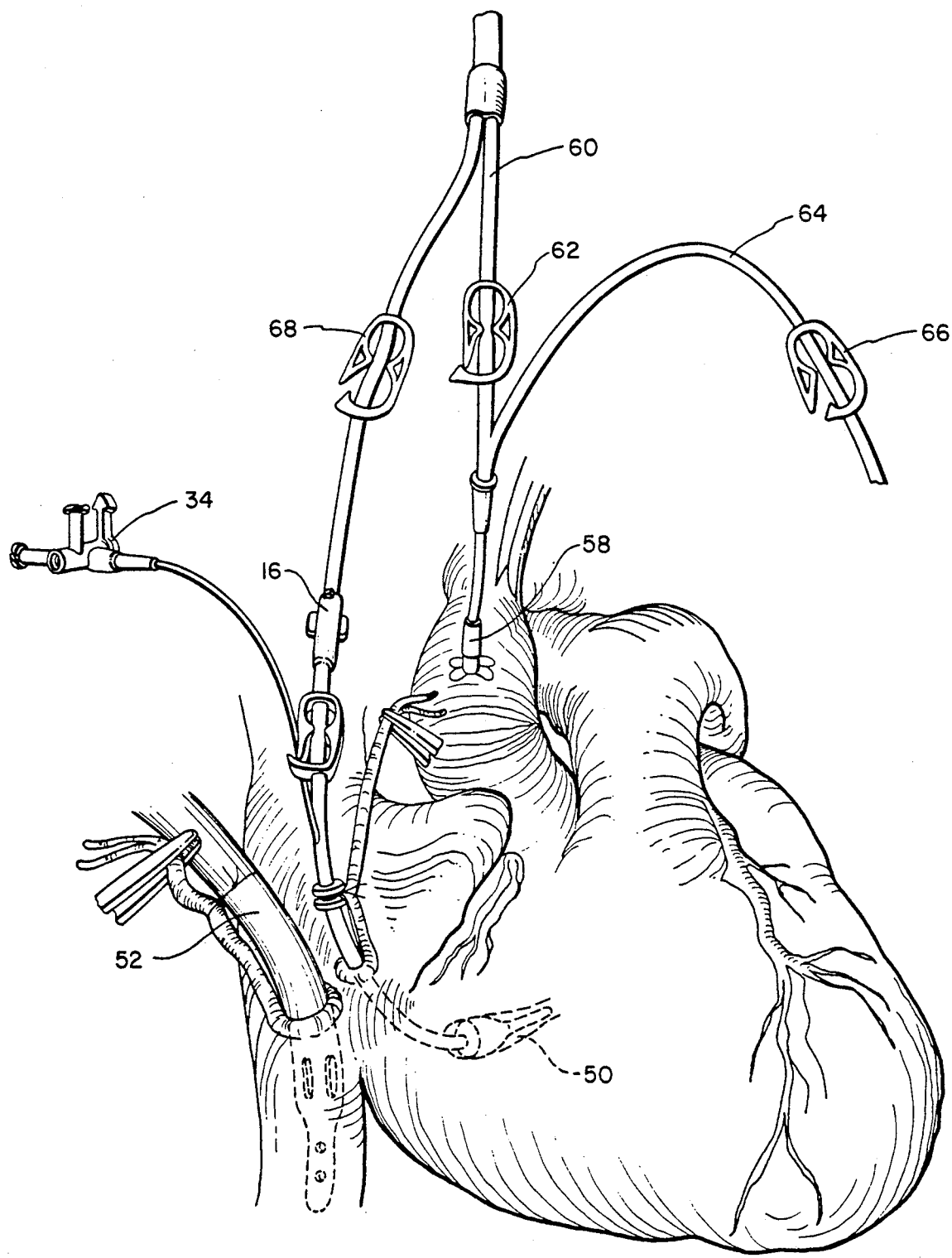
FIG. 5 is a perspective view illustrating a preferred embodiment of the present invention when used in combination with antegrade cardioplegia.

FIG. 5 illustrates one method of delivering antegrade and retrograde cardioplegia in combination. Antegrade catheter 58 is inserted according to the techniques of the prior art. Retrograde catheter 10 is inserted within the coronary sinus as described above. The initial infusion is made antegrade to achieve the most rapid arrest of the heart tissues supplied by unobstructed coronary arteries. Aortic infusion line 60 is clamped with aortic clamp 62 immediately after antegrade cardioplegia has been administered. Vent line 64 is then opened by releasing a vent clamp 66.

Retrograde clamp 68 is opened and retrograde cardioplegia is delivered via the coronary sinus to accomplish arrest and protection of regions supplied by constricted or occluded venous return of retrograde cardioplegic solution that flows into the right atrium through the thebesian channels. This protocol can be repeated during the surgical procedure when necessary for periodic infusion of cardioplegic solution.

C. Methods of Manufacturing the Self-filling Balloon

Figure 6:
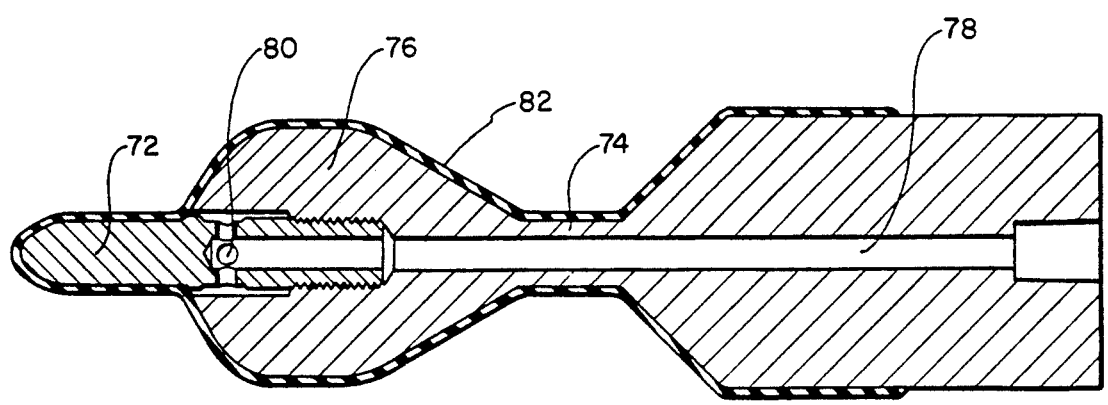
FIG. 6 is a cross-sectional view of a mandrel used in manufacturing a self-filling balloon within the scope of the present invention.

Unlike other balloons manufactured for use with balloon catheters, the balloon of the present invention does not stretch significantly past its original shape and size during use. Hence, the balloon of the present invention is to be distinguished from the typical prior art balloon catheters which are intended to inflate to several times their original size. Therefore, the balloon of the present invention is manufactured at approximately the size required for proper use. The balloon of the present invention is formed on a balloon mandrel having dimensions corresponding to the shape and size of the balloon. One such mandrel is illustrated in FIG. 6. Balloon mandrel 70 includes a mandrel tip 72 and a mandrel shank 74. Located between the mandrel tip and shank is balloon mold 76. The diameter of the mandrel tip and shank is approximately the same as the diameter of the s flexible cannula to which the balloon is to be ultimately securely attached.

To form a balloon, the balloon mandrel is dipped into a polymer solution which leaves a thin polymer coating on the mandrel surface. After the polymer has cured, the balloon is removed by peeling the thin coating off the mandrel.

The polymer should be capable of being placed in solution. However, the viscosity of the polymer solution affects the quality of the resulting balloon. If the viscosity is too high, then the balloon is too thick around those portions of the mandrel removed last from the solution. If the viscosity is too low, then the mandrel must be repeatedly dipped into the polymer solution to form a balloon thick enough for practical use. Such a thickness would be in the range from about 0.003 inches to about 0.005 inches with the presently preferred thickness being about 0.004 inches. The presently preferred viscosity of the polymer solution is about that of light honey.

The speed with which the mandrel is dipped into and removed from the polymer solution also affects the quality of the resulting balloon. If the mandrel is dipped too fast, then air bubbles are entrained within the polymer solution. If the mandrel is removed too fast, the polymer solution tends to drag on the mandrel surface leaving streaks of uneven thickness on the balloon. Dipping and removing the mandrel too slowly permits the polymer solution to evaporate, altering the viscosity of the solution. The time to dip the mandrel should be in the range from about 45 seconds to about 75 seconds, while the time to remove the mandrel should be in the range from about 135 seconds to about 165 seconds. The presently preferred time to dip the mandrel is about 60 seconds and the time to remove the mandrel is about 150 seconds.

It will be appreciated that in order to remove the balloon from the mandrel, the balloon portion formed around the mandrel shank must stretch to the balloon's maximum diameter. Thus, the polymer used to form the balloon must have excellent elongation properties, preferably with a percent elongation greater than about 600%. In addition, the shape of the balloon should not deform during its removal from the balloon mandrel.

Because the balloon is designed for in vivo use, it should preferably be constructed of a material which exhibits very low thrombogenicity. It has been found that the balloon may be suitably constructed of polyurethane. One preferred type of polyurethane is medical-grade TECOFLEX polyurethane, manufactured by Thermedics (Woburn, Massachusetts), which may be purchased in a solution form. More detailed information regarding this product is set forth in U.S. Pat. No. 4,447,590.

A quantity of polyurethane is preferably dissolved in tetrahydrofuran to form a solution having a concentration in the range from about 8% to about 9% polyurethane. This concentration results in a solution viscosity such that the mandrel is dipped into the solution three (3) times in order to achieve the desired balloon thickness.

Despite its apparent advantages, polyurethane possesses a high affinity for itself. Raw polyurethane tends to bind with raw polyurethane. The untreated surfaces of a newly formed balloon tend to bind together upon removal from the balloon mandrel, thereby resulting in a wrinkled, useless polyurethane mass. Therefore, in order to successfully construct balloons for use in the retrograde cardioplegia catheter of the present art with polyurethane, the balloon surfaces must be coated with a substance that will inhibit the self-affinity of polyurethane.

Several coating techniques known in the prior art have been considered and rejected as unsuitable. One such technique is to coat the mandrel with a powder, such as talcum powder, before dipping into the polyurethane solution. The resulting balloon contained trace amounts of talcum powder within the inner chamber. Because the balloon is self-filling, the risk of talcum powder being introduced into a patient's blood supply is considered unacceptable.

In another technique, the mandrel was coated with a thin layer of silicone prior to dipping the mandrel into the polyurethane solution. However, the resulting balloon s contained an uneven layer of polyurethane. This is likewise considered unacceptable.

Thus a principal problem in manufacturing the self-filling balloon within the scope of the present invention is to coat the inner surface of the balloon after the balloon had been formed, but before removal from the mandrel.

This problem is solved according to the present invention by injecting a coating agent through a borehole in the center of the mandrel such that the coating agent exits the mandrel at the juncture between mandrel tip 72 and balloon mold 76. The coating agent proceeds back along the surface of the balloon mold towards the mandrel shank until the entire inner surface of the balloon is coated.

As illustrated in FIG. 6, there is a hollow bore 78 through the center of the balloon mandrel. The mandrel tip, which is threadably attached to the balloon mold, also possesses a corresponding hollow bore which opens into two exit holes 80.

Figure 7:
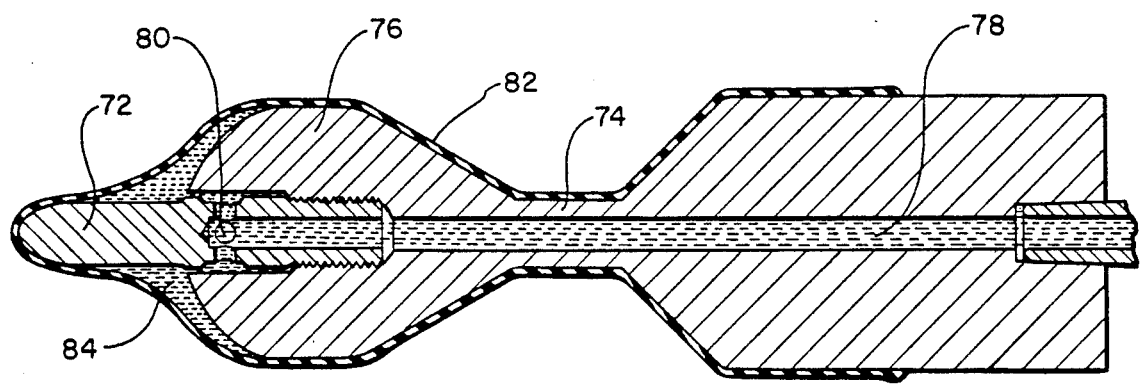
FIG. 7 is a cross-sectional view of the mandrel shown in FIG. 6 in which the balloon is beginning to separate from the mandrel due to the injection of a releasing fluid.

Referring now to FIG. 7, to release a balloon 82 formed around the periphery of the balloon mold, a coating agent 84 is injected through the hollow bore, through the exit holes, and out the juncture between the mandrel tip and balloon mold. The coating agent separates the balloon from the mandrel as it proceeds along the surface of the balloon mold.

One suitable coating agent is a solution silicone dissolved in freon having a concentration of silicone in the range from about 3% to about 10%. In one presently preferred embodiment, the silicone concentration in freon is about 5%. The freon rapidly evaporates leaving a thin film of silicone. The silicone also facilitates removal of the balloon by lubricating the mandrel. The same silicone/freon solution is preferably applied to the outer surface of the balloon to prevent self adhesion of the polyurethane.

Figure 8:
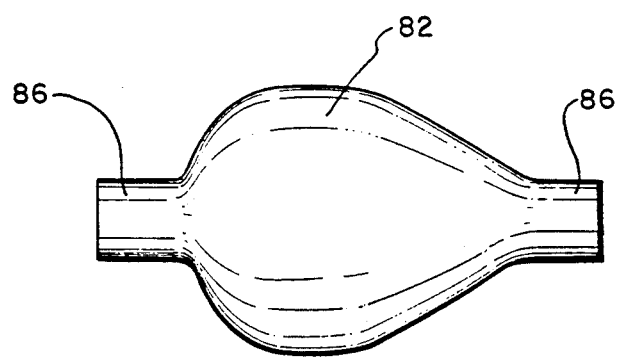
FIG. 8 is a plan view of a balloon removed from the mandrel and prepared for attachment to the flexible cannula.

FIG. 8 illustrates a balloon which has been removed from the mandrel and prepared for attachment to the cannula. In order to prepare the balloon for attachment to the cannula, the portions of the balloon formed around the mandrel tip and shank are cut leaving two sleeves 86, preferably about one eighth (⅛) inch long, extending from each end of the balloon. The sleeves are then preferably solvent bonded to the flexible cannula. As mentioned above, Tetrahydrofuran is the solvent of choice.

From the foregoing, it will be appreciated that the present invention provides apparatus and methods for performing retrograde cardioplegia which are simple and effective so that the advantages of retrograde cardioplegia can be readily utilized by surgeons.

Additionally, it will be appreciated that the present invention further provides apparatus and method for performing retrograde cardioplegia which do not require right atrial isolation, right atriotomy, and repeated cannulation of the apparatus.

Likewise, it will be appreciated that because the present invention provides a retrograde cardioplegia catheter which can be quickly and accurately inserted within the coronary sinus, the patient suffers relatively little trauma.

It will also be appreciated that the present invention provides apparatus and methods for performing retrograde cardioplegia which allow surgeons to safely use the life-saving internal mammary graft without making the surgical procedure cumbersome.

Finally, it will be appreciated that the present invention provides a method for manufacturing a self-filling balloon adapted for use with a retrograde cardioplegia catheter which can be safely and efficiently coated with an agent for preventing self adhesion.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A catheter for performing retrograde venous cardioplegia by delivering a cardioplegic solution into the coronary sinus of the heart, the catheter comprising:

a flexible, dual lumen cannula of a size capable of insertion into the coronary sinus of the heart, said cannula having an infusion lumen and a sensing lumen;

a balloon attached to the cannula periphery near the distal end of the cannula, thereby forming a chamber between the balloon and the cannula;

at least one balloon aperture in the infusion lumen positioned such that the infusion lumen is in communication with the chamber formed by the balloon and the cannula through the at least one balloon aperture, the aggregate of said balloon apertures having a total cross-sectional area which is greater than the cross-sectional area of the infusion lumen;

at least one infusion lumen outlet in the infusion lumen positioned between the balloon and the distal end of the cannula such that, when cardioplegic solution passes through the infusion lumen, a portion of the cardioplegic solution enters the chamber through the at least one balloon aperture and a portion of the cardioplegic solution exits the infusion lumen and the cannula through the at least one infusion lumen outlet, the aggregate of said infusion lumen outlets having a total cross-sectional area which is in the range of from about twenty-five percent to about seventy-five percent of the cross-sectional area of the infusion lumen, thereby creating a pressure within the infusion lumen which causes the cardioplegic solution to enter the chamber through the at least one balloon aperture in order to fill the balloon until it is turgid and in sealing engagement with the walls of the coronary sinus; and at least one sensing lumen orifice in the sensing lumen located at a point between the balloon and the distal end of the cannula which is remote from the at least one infusion lumen outlet, said sensing lumen orifice having a cross-sectional area greater than the cross-sectional area of the sensing lumen.

2. A catheter as defined in claim 1, further comprising a tip located at the distal end of the cannula such that the distal ends of the infusion lumen and the sensing lumen are occluded at the tip, the tip being configured and made of a material such that trauma to the coronary sinus is minimized during insertion of the cannula.

3. A catheter as defined in claim 2, wherein the tip located at the distal end of the cannula is constructed of a material having a softness in the range of about 55 to about 60 durometer, Shore-A.

4. A catheter as defined in claim 3, wherein the tip located at the distal end of the cannula is constructed of medical grade polyvinyl chloride.

5. A catheter as defined in claim 2, wherein the distal end of the balloon is located back from the tip a distance in the range from about 2 centimeters to about 6 centimeters.

6. A catheter as defined in claim 1, further comprising means attached to the proximal end of the infusion lumen for introducing the cardioplegic solution into and through the infusion lumen.

7. A catheter as defined in claim 6, further comprising means attached to the proximal end of the sensing lumen for sensing the pressure of the cardioplegic solution at the at least one sensing lumen orifice.

8. A catheter as defined in claim 6, further comprising means for stopping the introduction of the cardioplegic solution into the infusion lumen when the pressure of the cardioplegic solution exiting the at least one infusion lumen outlet exceeds a predetermined maximum pressure.

9. A catheter as defined in claim 1, wherein the balloon is tapered from the distal end to the proximal end of the balloon, thereby minimizing trauma during the insertion of the cannula into the coronary sinus and thereby encouraging the dealing engagement of the balloon with the walls of the coronary sinus.

10. A catheter as defined in claim 9, wherein the balloon taper is in the range from about 25° to about 35° measured from the longitudinal axis of the cannula.

11. A catheter as defined in claim 1, wherein the aggregate of said balloon apertures has a total cross-sectional area in the range of from about 1.5 to about 5 times the cross-sectional area of the infusion lumen.

12. A catheter as defined in claim 1, wherein the aggregate of said balloon apertures has a total cross-sectional area in the range from about 2 to about 3 times the cross-sectional area of the infusion lumen.

13. A catheter as defined in claim 1, wherein the balloon, when filled with cardioplegic solution, has a cross-sectional diameter in the range of from about 1.6 to about 2.0 centimeters.

14. A catheter as defined in claim 1, wherein the balloon when filled with cardioplegic solution, has a cross-sectional diameter in the range of from about 1.7 to about 1.8 centimeters.

15. A catheter as defined in claim 1, wherein the dual lumen cannula is constructed of a material having a softness in the range from about 75 to about 85 durometer, Shore-A.

16. A catheter as defined in claim 15, wherein the dual lumen cannula is constructed of medical grade polyvinyl chloride.

17. A catheter as defined in claim 1, wherein the balloon is constructed of a material having a percent elongation greater than about 600%.

18. A catheter as defined in claim 17, wherein the balloon is constructed of polyurethane.

19. A catheter as defined in claim 1, further comprising a plurality of balloon apertures in the infusion lumen.

20. A catheter as defined in claim 19, further comprising a plurality of infusion lumen outlets in the infusion lumen.

21. A catheter as defined in claim 20, wherein the balloon is tapered from the distal end to the proximal end of the balloon, thereby minimizing trauma during insertion of the cannula into the coronary sinus and thereby encouraging the sealing engagement of the balloon with the walls of the coronary sinus, said catheter further comprising:
   a tip located at the distal end of the cannula such that the distal ends of the infusion lumen and the sensing lumen are occluded at the tip, the tip being configured and made of a material such that trauma to the coronary sinus is minimized during insertion of the cannula.

22. A catheter as defined in claim 19, wherein the balloon is tapered from the distal end to the proximal end of the balloon, thereby minimizing trauma during insertion of the cannula into the coronary sinus and thereby encouraging the sealing engagement of the balloon with the walls of the coronary sinus, said catheter further comprising:
   a tip located at the distal end of the cannula such that the distal ends of the infusion lumen and the sensing lumen are occluded at the tip, the tip being configured and made of a material such that trauma to the coronary sinus is minimized during insertion of the cannula.

23. A catheter as defined in claim 1, further comprising a plurality of infusion lumen outlets in the infusion lumen.

24. A catheter as defined in claim 23, wherein the balloon is tapered from the distal end to the proximal end of the balloon, thereby minimizing trauma during insertion of the cannula into the coronary sinus and thereby encouraging the sealing engagement of the balloon with the walls of the coronary sinus, said catheter further comprising:
a tip located at the distal end of the cannula such that the distal ends of the infusion lumen and the sensing lumen are occluded at the tip, the tip being configured and made of a material such that trauma to the coronary sinus is minimized during insertion of the cannula.

25. A catheter as defined in claim 1, wherein the cross-sectional area of sensing lumen orifice is in the range from about 2 to about 3 times the cross-sectional area of the sensing lumen.

26. A catheter for performing retrograde venous cardioplegia by delivering a cardioplegic solution into the coronary sinus of the heart, the catheter comprising:
a flexible, dual lumen cannula of a size capable of insertion into the coronary sinus of the heart, said cannula having an infusion lumen and a sensing lumen;
a balloon attached to the cannula periphery near the distal end of the cannula, thereby forming a chamber between the balloon and the cannula;
at least one balloon aperture in the infusion lumen positioned such that the infusion lumen is in communication with the chamber formed by the balloon and the cannula through the at least one balloon aperture;
at least one infusion lumen outlet in the infusion lumen positioned between the balloon and the distal end of the cannula such that, when cardioplegic solution passes through the infusion lumen, a portion of the cardioplegic solution enters the chamber through the at least one balloon aperture and a portion of the cardioplegic solution exits the infusion lumen outlet, the aggregate of said infusion lumen outlets having a total cross-sectional area which is less than the total cross-section areas of the aggregate of said balloon apertures in the infusion lumen, thereby creating a pressure within the infusion lumen which causes the cardioplegic solution to enter the chamber through the at least one balloon aperture in order to fill the balloon until it is turgid and in sealing engagement with the walls of the coronary sinus;
at least one sensing lumen orifice in the sensing lumen located at a point between the balloon and the distal end of the cannula which is remote from the at least one infusion lumen outlet, said sensing lumen orifice having a cross-sectional area greater than the cross-sectional area of the sensing lumen; and
a stylet removably positioned within the flexible cannula, said stylet having a handle at the proximal end thereof and a predetermined curve at the distal end thereof, said stylet being constructed of a rigid material such that the stylet can be used to position the flexible cannula in the coronary sinus with minimal trauma to the heart tissues.

27. A catheter defined in claim 26, further comprising a tip located at the distal end of the cannula such that the distal ends of the infusion lumen and the sensing lumen are occluded at the tip, the tip being configured and made of a material such that trauma to the coronary sinus is minimized during insertion of the cannula.

28. A catheter as defined in claim 27, wherein the tip located at the distal end of the cannula is constructed of a material having a softness in the range of from about 55 to about 60 durometer, Shore-A.

29. A catheter as defined in claim 28, wherein the tip located at the distal end of the cannula is constructed of medical grade polyvinyl chloride.

30. A catheter as defined in claim 27, wherein the distal end of the balloon is located back from the tip a distance in the range from about 2 centimeters to about 6 centimeters.

31. A catheter as defined in claim 26, further comprising means attached to the proximal end of the infusion lumen for introducing the cardioplegic solution into and through the infusion lumen.

32. A catheter as defined in claim 31, further comprising means attached to the proximal end of the sensing lumen for sensing the pressure of the cardioplegic solution at the at least one sensing lumen orifice.

33. A catheter as defined in claim 31, further comprising means for stopping the introduction of the cardioplegic solution into the infusion lumen when the pressure of the cardioplegic solution exiting the at least one infusion lumen outlet exceeds a predetermined maximum pressure.

34. A catheter as defined in claim 26, wherein the balloon is tapered from the distal end to the proximal end of the balloon, thereby minimizing trauma during the insertion of the cannula into the coronary sinus and thereby encouraging the sealing engagement of the balloon with the walls of the coronary sinus.

35. A catheter as defined in claim 34, wherein the balloon taper is in the range from about 25° to about 35° measured from the longitudinal axis of the cannula.

36. A catheter as defined in claim 26, wherein the aggregate of said balloon apertures has a total cross-sectional area in the range of from about 1.5 to about 5 times the cross-sectional area of the infusion lumen.

37. A catheter as defined in claim 26, wherein the aggregate of said balloon apertures has a total cross-sectional area in the range from about 2 to about 3 times the cross-sectional area of the infusion lumen.

38. A catheter as defined in claim 26, wherein the balloon, when filled with cardioplegic solution, has a cross sectional diameter in the range of from about 1.6 to about 2.0 centimeters.

39. A catheter as defined in claim 26, wherein the balloon when filled with cardioplegic solution, has a cross-sectional diameter in the range of from about 1.7 to about 1.8 centimeters.

40. A catheter as defined in claim 26, wherein the dual lumen cannula is constructed of a material having a softness in the range from about 75 to about 85 durometer, Shore-A.

41. A catheter as defined in claim 40, wherein the dual lumen cannula is constructed of medical grade polyvinyl chloride.

42. A catheter as defined in claim 26, wherein the balloon is constructed of a material having a percent elongation greater than about 600%.

43. A catheter as defined in claim 42, wherein the balloon is constructed of polyurethane.

44. A catheter as defined in claim 26, further comprising a plurality of balloon apertures in the infusion lumen.

45. A catheter as defined in claim 44, wherein the distal end of the balloon is located back from the tip a distance in the range from about 2 centimeters to about 6 centimeters.

46. A catheter as defined in claim 45, wherein the balloon is tapered from the distal end to the proximal end of the balloon, thereby minimizing trauma during insertion of the cannula into the coronary sinus and thereby encouraging the sealing engagement of the balloon with the walls of the coronary sinus, said catheter further comprising:
a tip located at the distal end of the cannula such that the distal ends of the infusion lumen and the sensing lumen are occluded at the tip, the tip being configured and made of a material such that trauma to the coronary sinus is minimized during insertion of the cannula.

47. A catheter as defined in claim 44, wherein the balloon is tapered from the distal end to the proximal end of the balloon, thereby minimizing trauma during insertion of the cannula into the coronary sinus and thereby encouraging the sealing engagement of the balloon with the walls of the coronary sinus, said catheter further comprising:
a tip located at the distal end of the cannula such that the distal ends of the infusion lumen and the sensing lumen are occluded at the tip, the tip being configured and made of a material such that trauma to the coronary sinus is minimized during insertion of the cannula.

48. A catheter as defined in claim 26, further comprising a plurality of infusion lumen outlets in the infusion lumen.

49. A catheter as defined in claim 48, wherein the balloon is tapered from the distal end to the proximal end of the balloon, thereby minimizing trauma during insertion of the cannula into the coronary sinus and thereby encouraging the sealing engagement of the balloon with the walls of the coronary sinus, said catheter further comprising:
a tip located at the distal end of the cannula such that the distal ends of the infusion lumen and the sensing lumen are occluded at the tip, the tip being configured and made of a material such that trauma to the coronary sinus is minimized during insertion of the cannula.

50. A catheter as defined in claim 26, wherein the cross-sectional area of sensing lumen orifice is in the range from about 2 to about 3 times the cross-sectional area of the sensing lumen.

51. A catheter for performing retrograde venous cardioplegia by delivering a cardioplegic solution into the coronary sinus of the heart, the catheter comprising:
a flexible, dual lumen cannula of a size capable of insertion into the coronary sinus of the heart, said cannula having an infusion lumen and a sensing lumen;
a tip located at the distal end of the cannula such that the distal ends of the infusion lumen and the sensing lumen are occluded at the tip, the tip being configured and made of a material such that trauma to the coronary sinus is minimized during insertion of the cannula;
a balloon attached about and to the cannula periphery near the distal end of the cannula, thereby forming a chamber between the balloon and the cannula, said balloon being tapered from the distal end to the proximal end of the balloon, thereby minimizing trauma during the insertion of the cannula into the coronary sinus and thereby encouraging sealing engagement of the balloon with the walls of the coronary sinus;
a plurality of balloon apertures in the infusion lumen positioned such that the infusion lumen is in communication with the chamber formed by the balloon and the cannula through the balloon apertures, the aggregate of said balloon apertures having a total cross-sectional area in the range from about 1.5 to about 5 times the cross-sectional area of the infusion lumen;
a plurality of infusion lumen outlets in the infusion lumen positioned between the balloon and the distal end of the cannula such that, when cardioplegic solution passes through the infusion lumen, a portion of the cardioplegic solution enters the chamber through the balloon apertures and a portion of the cardioplegic solution exits the infusion lumen and the cannula through the infusion lumen outlets, the aggregate of said infusion lumen outlets having a total cross-sectional area which is in the range from about twenty-five to about seventy-five percent cross-section area of the infusion lumen, thereby creating a pressure within the infusion lumen which causes the cardioplegic solution to enter the inner chamber through the balloon apertures in order to fill the balloon until it is turgid and in sealing engagement with the walls of the coronary sinus;
at least one sensing lumen orifice in the sensing lumen located at a point between the balloon and the distal end of the cannula which is remote from the at least one infusion lumen outlet, said sensing lumen orifice having a cross-sectional area greater than the cross-sectional area of the sensing lumen; and
a stylet removably positioned within the flexible cannula, said stylet having a handle at the proximal end thereof, and a predetermined curve at the distal end thereof, said stylet being constructed of a rigid material such that the stylet can be used to position the flexible cannula in the coronary sinus with minimal trauma to the heart tissue.

52. A catheter as defined in claim 51, wherein the aggregate of said balloon apertures has a total cross-sectional area in the range from about 2 to about 3 times the cross-sectional area of the infusion lumen.

53. A catheter as defined in claim 51, wherein the balloon, when filled with cardioplegic solution, has a cross-sectional diameter in the range of from about 1.6 to about 2.0 centimeters.

54. A catheter as defined in claim 53, wherein the distal end of the balloon is located back from the tip a distance in the range from about 2 centimeters to about 6 centimeters.

55. A catheter as defined in claim 54, wherein the balloon is constructed of a material having a percent elongation greater than about 600%.

56. A catheter as defined in claim 55, wherein the balloon is constructed of polyurethane.

57. A catheter as defined in claim 54, wherein the balloon taper is in the range from about 25° to about 35° measured from: the longitudinal axis of the cannula.

58. A catheter as defined in claim 54, further comprising means attached to the proximal end of the infusion lumen for introducing the cardioplegic solution into and through the infusion lumen.

59. A catheter as defined in claim 58, further comprising means attached to the proximal end of the sensing lumen for sensing the pressure of the cardioplegic solution at the sensing lumen orifice.

60. A catheter as defined in claim 59, further comprising means for stopping the introduction of the cardioplegic solution into the infusion lumen when the pressure of the cardioplegic solution exiting the sensing lumen orifice exceeds a predetermined maximum pressure.

61. A catheter as defined in claim 54, wherein the tip located at the distal end of the cannula is constructed of a material having a softness in the range from about 55 to about 60 durometer, Shore-A.

62. A catheter as defined in claim 61, wherein the tip located at the distal end of the cannula is constructed of medical grade polyvinyl chloride.

63. A catheter as defined in claim 61, wherein the dual lumen cannula is constructed of a material having a softness in the range from about 75 to about 85 durometer, Shore-A.

64. A catheter as defined in claim 63, wherein the dual lumen cannula is constructed of medical grade polyvinyl chloride.

65. A catheter as defined in claim 51, wherein the balloon when filled with cardioplegic solution, has a cross-sectional diameter in the range of from about 1.7 to about 1.8 centimeters.

66. A catheter as defined in claim 51, wherein the cross-sectional area of sensing lumen orifice is in the range from about 2 to about 3 times the cross-sectional area of the sensing lumen.

67. A method for the retrograde administration of a cardioplegic solution into the coronary sinus of the heart, the method comprising the steps of:
   inserting a catheter through a small incision in the right atrium, said catheter comprising:
      a cannula having an infusion lumen with at least one infusion lumen outlet near its distal end such that cardioplegic solution can be introduced into and passed through the cannula and exit the outlet, said cannula also having a sensing lumen with a sensing lumen orifice near its distal end having a cross-sectional area greater than the cross-sectional area of the sensing lumen;
      a self-filling balloon secured about the cannula at a point proximal of the at least one infusion lumen outlet such that as cardioplegic solution passes through the cannula, a portion of the cardioplegic solution fills the balloon and a portion exits the cannula through the outlet; and
      a removable curved stylet located within the cannula, said stylet being constructed of a rigid material;
   manipulating the stylet to position the catheter within the coronary sinus such that the balloon, when filled with cardioplegic solution, will be in engagement with the walls of the coronary sinus;
   securing the catheter in place in order to minimize longitudinal movement of the balloon and outlet of cannula within the coronary sinus;
   withdrawing the stylet from within the catheter; and
   injecting cardioplegic solution through the cannula at sufficient pressure such that the balloon fills to sealingly engage the walls of the coronary sinus, thereby permitting retrograde administration of the cardioplegic solution.

68. A method for the retrograde administration of cardioplegic solution as defined in claim 67, further comprising the step of monitoring the pressure of the cardioplegic solution within the coronary sinus in order to minimize damage to the coronary sinus by excessive pressures and flow rates of the cardioplegic solution.

69. A method for the retrograde administration of a cardioplegic solution as defined in claim 68, further comprising the step of terminating the injection of the cardioplegic solution through the cannula if the fluid pressure within the coronary sinus exceeds a predetermined maximum pressure.

70. A method for the retrograde administration of cardioplegic solution as defined in claim 67, further comprising terminating the injection of the cardioplegic solution through the catheter such that the self-filling balloon empties to permit normal venous fluid flow into the right atrium.

71. A method for the retrograde administration of a cardioplegic solution as defined in claim 70, further comprising the step of periodically injecting cardioplegic solution through the cannula and terminating the injection of the cardioplegic solution.

72. A method for the retrograde administration of a cardioplegic solution as defined in claim 70, wherein after terminating the injection of the cardioplegic solution, antegrade cardioplegia is initiated for a period of time.

73. A method for the retrograde administration of a cardioplegic solution as defined in claim 67, further comprising the step of maintaining the fluid pressure within the coronary sinus below about 50 mmHg.

74. A method for the retrograde administration of a cardioplegic solution as defined in claim 67, wherein the cardioplegic solution is injected through the cannula at a flow rate in the range from about 200 ml/min to about 300 ml/min.

75. A catheter for performing retrograde venous cardioplegia by delivering a cardioplegic solution into the coronary sinus of the heart, the catheter comprising:
   a flexible, dual lumen cannula of a size capable of insertion into the coronary sinus of the heart, said cannula having an infusion lumen and a sensing lumen;
   a balloon attached to the cannula periphery near the distal end of the cannula, thereby forming a chamber between the balloon and the cannula;
   at least one balloon aperture in the infusion lumen positioned such that the infusion lumen is in communication with the chamber formed by the balloon and the cannula through the at least one balloon aperture, the aggregate of said balloon apertures having a total cross-sectional area which is greater than the cross-sectional area of the infusion lumen;
   at least one infusion lumen outlet in the infusion lumen positioned between the proximal end of the balloon and the distal end of the cannula such that, when cardioplegic solution passes through the infusion lumen, the size and configuration of the at least one infusion outlets creates a pressure within the infusion lumen which cause the cardioplegic solution enters the chamber through the at least one balloon aperture in a order to fill the balloon until it is turgid and in sealing engagement with the walls of the coronary sinus; and
   at least one sensing lumen orifice in the sensing lumen located at a point proximal of the distal end of the cannula which is remote from the at least one infusion lumen outlet, the aggregate of said sensing lumen orifices having a cross-sectional area greater than the cross-sectional area of the sensing lumen.

76. A method for the retrograde administration of a cardioplegic solution into the coronary sinus of the heart, the method comprising the steps of:

(a) inserting a catheter through a small incision in the right atrium, said catheter comprising:

a cannula having an infusion lumen with at least one infusion lumen outlet near its distal end such that cardioplegic solution can be introduced into and passed through the cannula and exit the outlet, said cannula also having a sensing lumen with at least one sensing lumen orifice near its distal end, the aggregate of said sensing lumen orifices having a total cross-sectional area greater than the cross-sectional areas of the sensing lumen;

a self-filling balloon secured about the cannula at a point proximal of the at least one infusion lumen outlet such that as cardioplegic solution passes through the cannula, a portion of the cardioplegic solution fills the balloon and a portion exits the cannula through the outlet; and a removable curved stylet located within the cannula;

(b) manipulating the stylet to position the catheter within the coronary sinus such that the balloon, when filled with cardioplegic solution, will be in engagement with the walls of the coronary sinus;

(c) securing the catheter in place in order to minimize longitudinal movement of the balloon and outlet of cannula within the coronary sinus;

(d) withdrawing the stylet from within the catheter; and (e) injecting cardioplegic solution through the cannula at sufficient pressure such that the balloon fills to sealingly engage the walls of the coronary sinus, thereby permitting retrograde administration of the cardioplegic solution.

77. A catheter for performing retrograde venous cardioplegia by delivering a cardioplegic solution into the coronary sinus of the heart, the catheter comprising:

a flexible, cannula of a size capable of insertion into the coronary sinus of the heart, said cannula having an infusion lumen and a sensing lumen;

a balloon attached to the cannula periphery near the distal end of the cannula, thereby forming a chamber between the balloon and the cannula;

at least one balloon aperture in the infusion lumen positioned such that the infusion lumen is in communication with the chamber formed by the balloon and the cannula through the at least one balloon aperture;

at least one infusion lumen outlet in the infusion lumen positioned between the proximal end of the balloon and the distal end of the cannula such that, when cardioplegic solution passes through the infusion lumen, the size and configuration of the at least one infusion outlets creates a pressure within the infusion lumen which causes the cardioplegic solution enters the chamber through the at least one balloon aperture in a order to fill the balloon until it is turgid and in sealing engagement with the walls of the coronary sinus;

at least one sensing lumen orifice in the sensing lumen located at a point proximal of the distal end of the distal end of the cannula which is remote from the at least one infusion lumen outlet, the aggregate of said sensing lumen orifices having a cross-sectional area greater than the cross-sectional area of the sensing lumen; and a stylet removably positioned within the flexible cannula, said stylet having a handle at the proximal end thereof and a predetermined curve at the distal end thereof, said stylet handle having a finger loop extending from the distal end of the stylet handle and a thumb rest located at the proximal end of the stylet handle.

78. A catheter for performing retrograde venous cardioplegia as defined in claim 77, wherein the stylet handle is configured such that placement of a surgeon's index finger against the finger loop, the ring finger against the stylet handle, and the thumb against the thumb rest enables the catheter to be quickly inserted with the coronary sinus with a slight twist of the surgeon's wrist.

79. A catheter for performing retrograde venous cardioplegia as defined in claim 77, wherein the stylet handle is configured such that placement of a surgeon's index finger against the finger loop, the ring finger against the stylet handle, and the thumb against the thumb rest enables the catheter to be quickly inserted with the coronary sinus with a slight twist of the surgeon's wrist.

* * * * *

UNITED STATES PATENT AND TRADEMARK OFFICE
CERTIFICATE OF CORRECTION

PATENT NO. : 5,021,045

DATED : June 4, 1991

INVENTOR(S) : Gerald D. Buckberg et al.

It is certified that error appears in the above-identified patent and that said Letters Patent is hereby corrected as shown below:

```
      Column 1, line 22, delete "s"
      Column 1, line 42, "cell s ability" should be --cell's ability--
      Column 1, line 48, delete "s"
      Column 2, line 46, "the heart After" should be ---the heart. After--
      Column 2, line 66, after "which" insert --pumps the blood
into the aorta above an aortic clamp. Then,--
      Column 4, line 56, "principle reason" should be --principal
reason--
      Column 5, lines 54-55, after "catheter" insert --.--
      Column 7, line 48, after "coronary" insert --sinus from
inadvertent puncture. Yet the flexible cannula--
      Column 8, line 22, "a bout" should be --about--
      Column 9, line 17, "current" should be --currently--
      Column 9, line 23, after "of the" insert --coronary sinus.
However, during infusion of the--
      Column 9, line 40, after "illustrated" insert --in--
      Column 11, line 2, "," should be --;--
      Column 12, line 12, "are" should be --is--
      Column 14, line 4, after "occluded" insert --coronary arteries.
Venous return catheter 52 captures the--
      Column 14, line 19, "The balloon of the . . . attached." should
begin a new paragraph
      Column 15, line 43, "s" should be deleted
      Column 19, line 41, after "lumen" insert --and the cannula through
the at least one infusion lumen--
      Column 24, line 61, "outlets creates" should be --outlet creates--
      Column 24, line 62, "cause" should be --causes--
      Column 24, line 63, "enters" should be --to enter--
```

UNITED STATES PATENT AND TRADEMARK OFFICE
CERTIFICATE OF CORRECTION

PATENT NO. : 5,021,045

DATED : June 4, 1991

INVENTOR(S) : Gerald D. Buckberg et al.

It is certified that error appears in the above-identified patent and that said Letters Patent is hereby corrected as shown below:

Column 26, line 14, "outlets creates" should be --outlet creates--
Column 26, line 16, "enters" should be --to enter--
Column 26, line 21, "proximal of the distal end of the distal end" should be --between the balloon and the distal end--
Column 26, line 45, "index finger" should be --ring finger--
Column 26, line 45, "ring finger" should be --index finger--

Signed and Sealed this

Eighth Day of June, 1993

Attest:

MICHAEL K. KIRK

*Attesting Officer*  *Acting Commissioner of Patents and Trademarks*